(12) United States Patent
Pelissier et al.

(10) Patent No.: US 9,408,587 B2
(45) Date of Patent: Aug. 9, 2016

(54) HIGHLY CONFIGURABLE MEDICAL ULTRASOUND MACHINE AND RELATED METHODS

(75) Inventors: Laurent Pelissier, Vancouver (CA); Bill Zhang, Richmond (CA); Tomas Bobovsky, Richmond (CA)

(73) Assignee: Ultrasonix Medical Corporation, Richmond, CA (US)

( * ) Notice: Subject to any disclaimer, the term of this patent is extended or adjusted under 35 U.S.C. 154(b) by 1370 days.

(21) Appl. No.: 12/545,742

(22) Filed: Aug. 21, 2009

(65) Prior Publication Data

US 2010/0049050 A1   Feb. 25, 2010

Related U.S. Application Data

(60) Provisional application No. 61/091,285, filed on Aug. 22, 2008.

(51) Int. Cl.
*A61B 8/00* (2006.01)
*G06F 19/00* (2011.01)

(52) U.S. Cl.
CPC . *A61B 8/00* (2013.01); *A61B 8/463* (2013.01); *A61B 8/465* (2013.01); *A61B 8/467* (2013.01); *A61B 8/585* (2013.01); *G06F 19/321* (2013.01)

(58) Field of Classification Search
CPC ........ A61B 8/467; A61B 8/585; A61B 8/463; A61B 8/00; A61B 8/465
USPC .......................................... 600/437, 443, 459
See application file for complete search history.

(56) References Cited

U.S. PATENT DOCUMENTS

| | | | |
|---|---|---|---|
| 5,715,487 A * | 2/1998 | McIntyre et al. | 396/299 |
| 6,488,629 B1 | 12/2002 | Saetre et al. | |
| 6,656,119 B2 * | 12/2003 | Sasaki et al. | 600/437 |
| 6,689,055 B1 * | 2/2004 | Mullen et al. | 600/300 |
| 7,221,972 B2 | 5/2007 | Jackson et al. | |
| 7,244,230 B2 * | 7/2007 | Duggirala et al. | 600/300 |
| 2003/0097065 A1 * | 5/2003 | Lee et al. | 600/437 |
| 2003/0105399 A1 * | 6/2003 | Morsy et al. | 600/437 |
| 2004/0179332 A1 * | 9/2004 | Smith et al. | 361/681 |
| 2005/0054927 A1 * | 3/2005 | Love | 600/443 |
| 2005/0165096 A1 * | 7/2005 | Lee | 514/534 |
| 2005/0251036 A1 * | 11/2005 | Abuhamad | 600/437 |

(Continued)

FOREIGN PATENT DOCUMENTS

WO   WO 2007036880 A1 *   4/2007

OTHER PUBLICATIONS

Atherosclerosis Risk in Communities Study Protocol, Manual 6a, Ultrasound Assessment; Scanning Procedures, Visit 3, Version 3.0, ARIC Coordinating Center, Department of Biostatistics, UNC Chapel Hill, Jan. 1995.*

*Primary Examiner* — James Kish
*Assistant Examiner* — Saurel J Selkin
(74) *Attorney, Agent, or Firm* — Anthony M. Del Zoppo, III; Driggs, Hogg, Daugherty & Del Zoppo, Co., LPA

(57) ABSTRACT

An ultrasound machine is operated by executing a protocol. Executing the protocol configures the ultrasound machine, controls for operating the ultrasound machine and a display for the ultrasound machine. Protocols may be defined to provide a streamlined configuration of controls for operating the ultrasound machine, and to provide instructions that guide a user's operation of the ultrasound machine.

26 Claims, 10 Drawing Sheets

(56) References Cited

U.S. PATENT DOCUMENTS

| | | |
|---|---|---|
| 2007/0081705 A1* | 4/2007 | Carneiro et al. .............. 382/128 |
| 2007/0232907 A1 | 10/2007 | Pelissier et al. |
| 2008/0097205 A1* | 4/2008 | Takimoto et al. ............. 600/437 |
| 2009/0093719 A1 | 4/2009 | Pelissier et al. |
| 2009/0099449 A1* | 4/2009 | Lundberg ...................... 600/443 |
| 2009/0198132 A1 | 8/2009 | Pelissier et al. |

* cited by examiner

HIGHLY CONFIGURABLE MEDICAL ULTRASOUND MACHINE AND RELATED METHODS

REFERENCE TO RELATED APPLICATION

This application claims the benefit under 35 U.S.C. §119 of U.S. patent application No. 61/091,285 filed 22 Aug. 2008 and entitled "HIGHLY CONFIGURABLE MEDICAL ULTRASOUND MACHINE AND RELATED METHODS", which is hereby incorporated by reference herein.

TECHNICAL FIELD

This invention relates to medical ultrasound machines which can be configured to perform specific ultrasound data acquisition and/or measurement tasks. Embodiments of the invention provide ultrasound machines configured to acquire one or more ultrasound images and/or measurements according to a previously-defined ultrasound protocol.

BACKGROUND

Modern ultrasound machines can operate in a range of imaging modes. In any imaging mode, the operation of an ultrasound machine can be adjusted by setting various parameters. The parameters can affect things such as the nature of acoustic signals emitted by the ultrasound machine, the way received echo signals are processed, and the way that ultrasound images are created and displayed. An ultrasound machine typically has a large number of controls that can be used to set the operating mode of the ultrasound machine and the parameters that will affect the operation of the ultrasound machine in that mode. This can be confusing, especially for inexperienced operators.

There is a need for ultrasound machines that are simple to operate. There is a particular need for ultrasound machines that are capable of sophisticated ultrasound imaging operations and are simple to operate.

SUMMARY OF THE INVENTION

The invention has a variety of aspects. Aspects of the invention provide apparatus for operating ultrasound machines, apparatus for defining protocols for operating ultrasound machines and methods for operating ultrasound machines displays, controller for displays and methods for controlling displays.

In one method aspect, a method is provided for operating an ultrasound machine comprising the steps of: defining a protocol; making the protocol available to the ultrasound machine; invoking the protocol; and executing the protocol; wherein the protocol comprises a setup and the setup comprises a configuration of the ultrasound machine, a configuration of controls for operating the ultrasound machine, and a configuration of a display for the ultrasound machine.

In a related method aspect, the step of defining the protocol comprises the steps of performing an ultrasound exam using an ultrasound machine, the exam comprising one or more procedures; recording the controls used for operating the ultrasound machine during the one or more procedures; generating a draft protocol comprising one or more draft setups, each draft setup comprising a configuration of controls for operating the ultrasound machine that comprises the controls used during a corresponding procedure; and determining for each draft setup whether each of the controls used during the corresponding procedure should be fixed or should be user-controllable.

In an apparatus aspect, apparatus is provided for operating an ultrasound machine comprising a protocol controller configured to execute a protocol to configure the ultrasound machine, configure controls for operating the ultrasound machine, and configure a display for the ultrasound machine.

In another apparatus aspect, apparatus is provided for defining protocols for operating an ultrasound machine comprising a display, wherein the display comprises graphical representations for a range of available controls for operating the ultrasound machine and an authoring area into which a user can introduce and arrange controls for operating the ultrasound machine.

Further aspects of the invention and feature of embodiments of the invention are described below and illustrated in the accompanying drawings.

BRIEF DESCRIPTION OF DRAWINGS

Non-limiting example embodiments are illustrated in the appended drawings.

DETAILED DESCRIPTION

Figure 1:
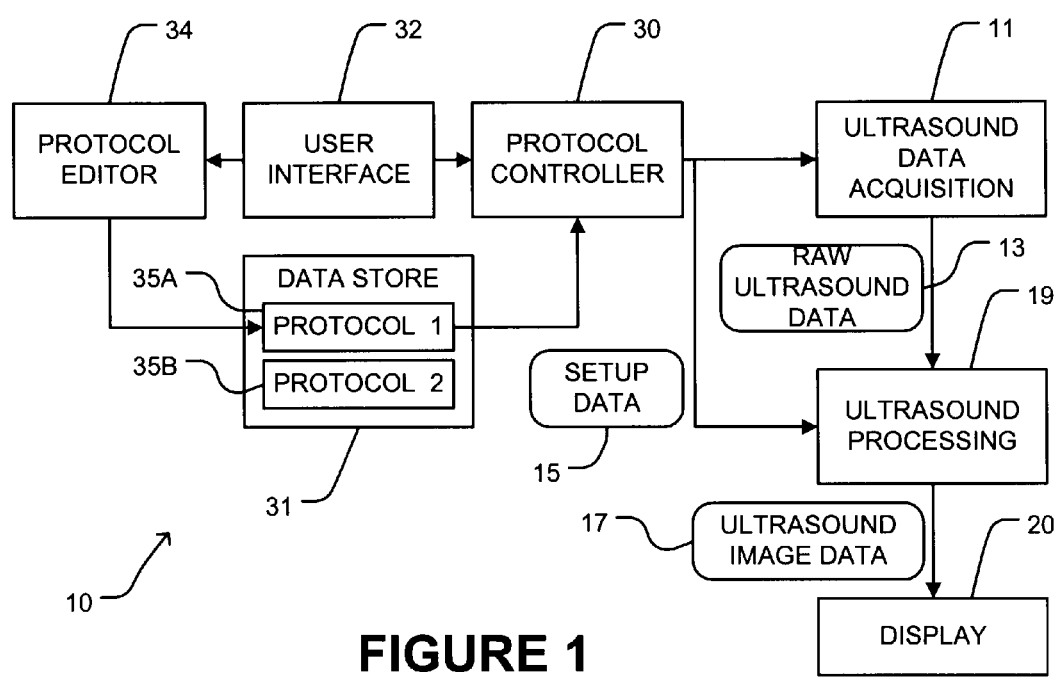
FIG. 1 is a block diagram illustrating a medical ultrasound machine according to an example embodiment of the invention.
Figure 1A:
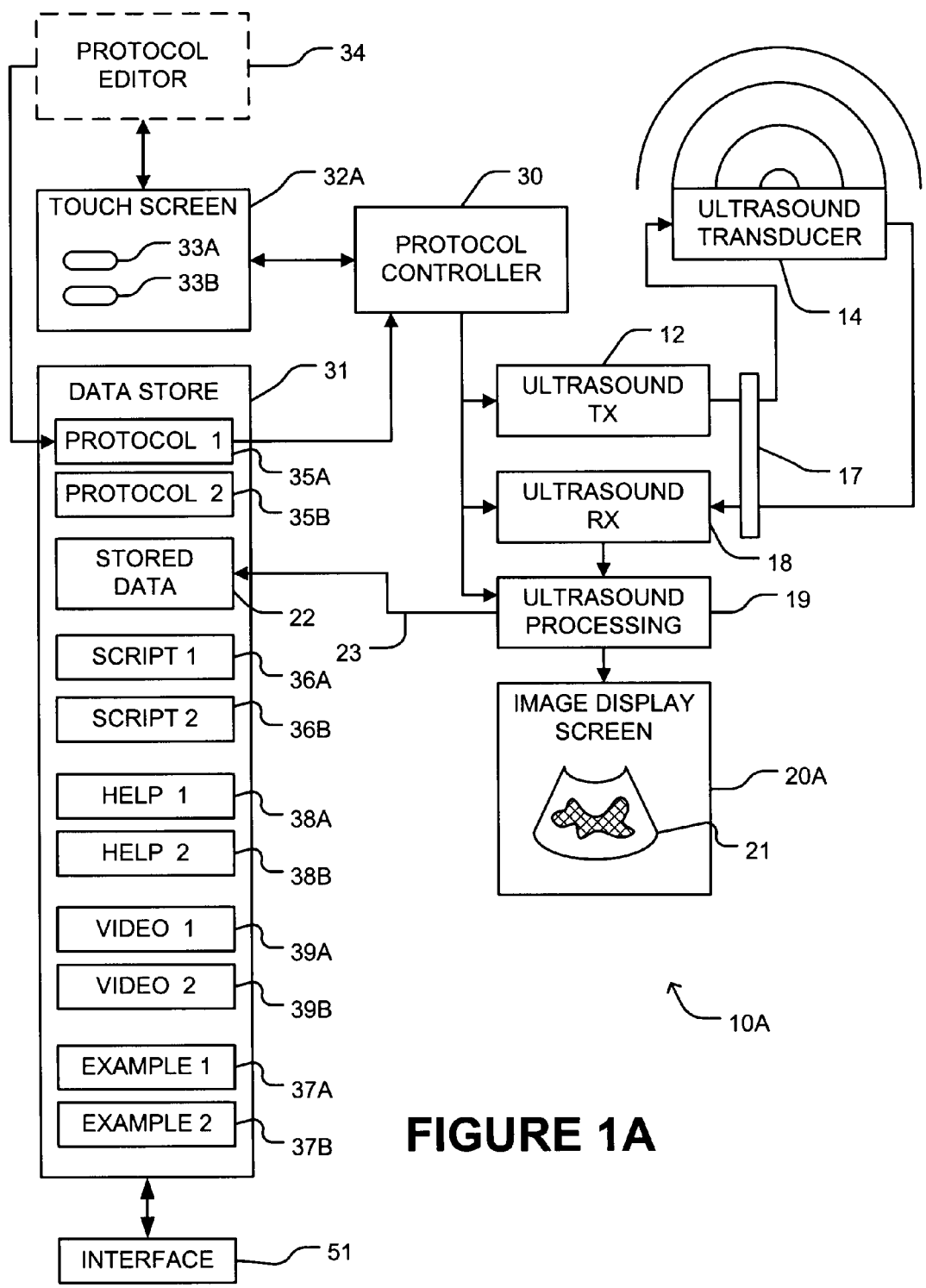
FIG. 1A is a block diagram illustrating a medical ultrasound machine according to another example embodiment of the invention.

FIG. 1 is a block diagram of an ultrasound machine 10 according to an example embodiment. FIG. 1A is a more specific block diagram of an ultrasound machine 10A according to a specific example embodiment.

Referring to FIG. 1, machine 10 includes an ultrasound data acquisition stage 11 which acquires raw ultrasound data 13. Ultrasound data acquisition stage 11 may include, for example, a number of probes, each comprising an array of transducer elements. Raw ultrasound data 13 may comprise digitized ultrasound signals. Ultrasound data acquisition stage 11 provides raw ultrasound data 13 to an ultrasound processing stage 19. Ultrasound processing stage 19 processes raw ultrasound data 13 to produce ultrasound image data 17, which is provided to a display 20.

Ultrasound machine 10 includes a protocol controller 30. Protocol controller 30 can set the configurations of other parts of ultrasound machine 10. In the embodiment of FIG. 1, protocol controller 30 provides setup data 15 to ultrasound data acquisition stage 11 and ultrasound processing stage 19.

For example, protocol controller 30 can control how ultrasound data acquisition stage 11 transmits ultrasound signals in order to:
provide different types of beamforming,
generate signals for different subsets of transducer elements of a given probe;
generate signals suitable for driving the transducer elements of different probes;
generate set of signals for driving different numbers of transducer elements and/or different geometries;
adjust the intensity of acoustic pulses to be delivered;
adjust the waveforms of signals used to generate the pulses;
adjust the phasing of signals to be used for driving different sets of transducer elements;
etc.
Similarly, protocol controller 30 can control ultrasound data acquisition stage 11 to process received ultrasound signals to generate raw ultrasound data 13 in various ways. For example, protocol controller 30 may have access to:
set the gain of amplification stages;
set cut-off frequencies, knee points, and other parameters for filters;
etc.
within the range of adjustment provided for in ultrasound data acquisition stage 11. Protocol controller 30 may also have access to alter the ultrasound processing performed in ultrasound processing stage 19 to create a desired type of image based upon the received ultrasound signals. For example, protocol controller 30 may have access to select from among various ultrasound processing algorithms and to set parameters for a selected algorithm.

Protocol controller 30 may comprise software executing on a programmable data processor. The software may cause the data processor to place ultrasound machine 10 in a desired operational state by writing parameters or other values to control registers that determine the state of the ultrasound machine 10, loading or pointing to specific software components for execution by processors of ultrasound machine 10 and/or configuring images and other information to be displayed on displays associated with ultrasound machine 10.

Protocol controller 30 is connected to a data store 31 which may contain a number of setup files 35 (individually numbered 35A, 35B, etc.). Each setup file 35 specifies a particular configuration for ultrasound machine 10. Protocol controller 30 can place ultrasound machine 10 in a desired configuration by retrieving a setup file 35 that specifies the desired configuration from data store 31 and then configuring the ultrasound machine 10 according to information in the retrieved setup file.

Ultrasound machine 10 also includes a protocol editor 34 and a user interface 32 for interacting with protocol controller 30 and protocol editor 34. A user may edit setup files 35 and other files stored in data store 31 using protocol editor 34, and may cause ultrasound machine 10 to execute protocols using protocol controller 34.

Referring to FIG. 1A, ultrasound machine 10A includes an ultrasound transmitter stage 12 which comprises or may be configured to provide a beamformer. Ultrasound transmitter stage 12 delivers driving signals to an ultrasound transducer 14 comprising an array of elements. Transducer 14 may also sometimes be referred to as a "probe". The elements of transducer 14 may comprise piezoelectric elements for example. Transducer 14 may be coupled to the rest of machine 10A by a suitable connector 17. In alternative embodiments for specialized applications transducer 14 could be hard wired to ultrasound machine 10A.

Ultrasound transmitter stage 12 causes the elements of transducer 14 to emit acoustic signals. The intensity, phasing, waveforms, and other characteristics of the acoustic signals are determined by the configuration of ultrasound transmitter stage 12.

Ultrasound machine 10A includes transducer elements that detect the acoustic signals after the acoustic signals have interacted with structures inside a subject's body. In the illustrated embodiment, the elements act both as transducers that generate acoustic signals and as transducers that receive acoustic signals and convert the received acoustic signals into electrical signals. Separate sets of transducers could be used for transmitting and receiving ultrasound.

Acoustic signals detected at transducer 14 are provided to an ultrasound receiver stage 18. Ultrasound receiver stage 18 performs some processing on received signals and passes the result to ultrasound processing stage 19. In some embodiments, ultrasound receiver stage 18 includes signal conditioning electronics, such as amplifiers, filters, and the like. Received signals are digitized in ultrasound receiver stage 18 and the digitized signals are passed to ultrasound processing stage 19. Processing of received ultrasound signals may be divided between stages 18 and 19 in any suitable ways. In some embodiments, ultrasound receiver stage 14 provides processing primarily in the analog domain while ultrasound processing stage 19 provides processing primarily in the digital domain. In some embodiments ultrasound processing stage 19 includes a data processor that is programmed to process signals received from ultrasound receiver stage 18.

An image 21 generated by ultrasound processing stage 19 may be displayed on an image display screen 20A of ultrasound machine 10A.

Ultrasound machine 10A also includes a protocol controller 30 and a protocol editor 34, as discussed above in reference to ultrasound machine 10 of FIG. 1. In some embodiments, protocol editor 34 may be provided in a device which is separate from ultrasound machine 10A, as indicated by the dashed box used to represent protocol editor 34 in FIG. 1A.

In example ultrasound machine 10A of FIG. 1A, the user interface comprises a touch screen 32A. Touchscreen 32A can display different controls 33 (individually numbered 33A, 33B, etc.). Controls 33 can be actuated by a user in order to control operation of ultrasound machine 10A in a way corresponding to the control. In some embodiments, protocol controller 30 determines which controls 33 are displayed on touchscreen 32A at any given time. In some embodiments, the locations and/or appearances of the controls 33 being displayed are set by protocol controller 30.

As discussed above with respect to ultrasound machine 10, protocol controller 30 and protocol editor 34 of ultrasound machine 10A are connected to a data store 31 which may contain a number of setup files 35 (individually numbered 35A, 35B, etc.). Each setup file 35 specifies a particular configuration for ultrasound machine 10A. Protocol controller 30 can place ultrasound machine 10A in a desired configuration by retrieving a setup file 35 that specifies the desired configuration from data store 31 and then configuring the ultrasound machine 10A according to information in the retrieved setup file 35. Protocol editor 34 can be used, through touchscreen 32A, to edit setup files 35 or other files stored in data store 31. In the illustrated embodiment, setup files 35 include information that defines the controls 33 to be displayed on a touchscreen 32A for a configuration specified by the setup file 35 and the locations in which those controls are to be displayed on touchscreen 32A.

Protocol controller 30 may execute a script which causes ultrasound machine 10A to be placed in a succession of different configurations and to acquire and store and/or display ultrasound data for each of the configurations. Ultrasound data 23 generated by ultrasound processing stage 19 may be stored in a memory area 22 that is in or accessible to ultrasound machine 10. As discussed in more detail below, in executing the script, protocol controller 30 may cause prompts and other information to be displayed for the assistance of a user.

In the illustrated embodiment, a number of script files 36 (individually numbered 36A, 36B etc.) containing different scripts are available to protocol controller 30 in data store 31. Script files 36 contain instructions which cause protocol controller 30 to perform a sequence of actions including configuring ultrasound machine 10 according to at least one setup file 35.

It can be appreciated that an ultrasound machine 10 or 10A, as described herein, may be configured in a way that is very useful for a novice ultrasound machine user. For example, consider the case where a protocol requires a user to acquire a sequence of ultrasound images of various internal organs of a subject. The protocol may also require the user to make certain measurements of anatomical features imaged in the images. An ultrasound machine 10 or 10A may be equipped with a script which is executed by protocol controller 30. The script may cause protocol controller 30 to place ultrasound machine 10 or 10A in a configuration suitable for acquiring a first image required by the protocol. At the same time a prompt is displayed on display 20 of machine 10 or touch-screen 32A and/or image display screen 20A of machine 10A. The prompt may instruct the operator to acquire the image in question and may contain additional information. For example, the prompt may include an image showing how to apply a transducer to acquire the ultrasound image in question. The prompt may include other information such as a particular transducer to use, how to make a particular measurement, or the like.

Additional help may be provided in the form of context-sensitive help screens 38 (individually numbered 38A, 38B etc.) or context-sensitive video presentations 39 (individually numbered 39A, 39B etc.), as shown in FIG. 1A. A help screen 38 and/or a video presentation 39 may be associated with each setup of ultrasound machine 10A. Touch screen 32A may be configured to display controls which permit a user to view the associated help screen 38 and/or the associated video 39. For example, where a setup configures ultrasound machine 10A to acquire a transverse image of a subject's liver, a corresponding help screen 38 may include a description of how to apply the probe to acquire the necessary image and may have some photographs or drawings which illustrate this. A corresponding video 39 may show a short video clip of a good way to acquire suitable transverse images of the liver.

One or more example images 37 (individually numbered 37A, 37B etc.) may be associated with each setup. The example image 37 may, for example, show an image having an acceptable contrast and the like. A user can compare the example image with the image being shown on image display screen 20A to determine whether the acquired image 21 is of the correct anatomical structure and is generally satisfactory. Optionally example images 37 may be provided that show unacceptable views as well. In some embodiments the example image is shown together with image 21 on one or both of touch screen 32A and image display screen 20A so that the example image and acquired image can be readily compared.

Therefore, for each setup specified by the script, the user may be informed regarding what the user is required to do. Additionally, since protocol controller 30 controls the controls 33 to be displayed on touch screen 32A, only the controls required for the current setup need to be displayed on touch screen 32A. Controls that are not required can be omitted. Furthermore, the main control that may be required to make an adjustment, take a measurement, or the like may be displayed consistently in a convenient main control area on touch screen 32A. For each setup, the user can readily locate the particular control that is most important for the current step in the protocol by looking at the main control area. Thus, by following instructions, a user can step through a protocol of any length or complexity.

A protocol may define activities that need to occur between different setups. For example, different setups may require different probes. A protocol may require that a probe be changed between different setups. In some embodiments, the protocol may display a request that the probe be changed. The protocol can indicate the required probe (and show a picture or other identifying information for the required probe) and include instructions on how to change the probe. The ultrasound device may detect automatically when the required probe has been attached (in cases where the ultrasound machine can auto-detect the type of connected probe). In other embodiments, the protocol may request user input confirming that the required probe has been located and connected to the machine.

This functionality permits a protocol to conduct an examination which may involve using a first probe operating in a first mode to obtain one or more results and then switching to using a second probe operating in a second mode to obtain one or more further results etc.

A protocol may comprise a sequence of steps. The steps may include:
  machine configuration steps (which configure an ultrasound machine appropriately for subsequent steps);
  data acquisition steps;
  measurement and display steps;
  data storing steps;
  steps which prompt a user to take specific actions; and
  steps which provide context-dependent help information. The help information may include things such as example images, video demonstrations, help text, and troubleshooting hints. The example images may be taken on the identical type of machine operating in the identical mode.

In some embodiments, a help desk control is provided. When a user invokes the help desk control the current image as well as information regarding the current setup and information regarding the subject is electronically forwarded by way of a suitable wired or wireless data communication network to a terminal manned by a person who can provide advice to the user or confirm whether or not an acquired image of video sequence is acceptable.

Figure 2:
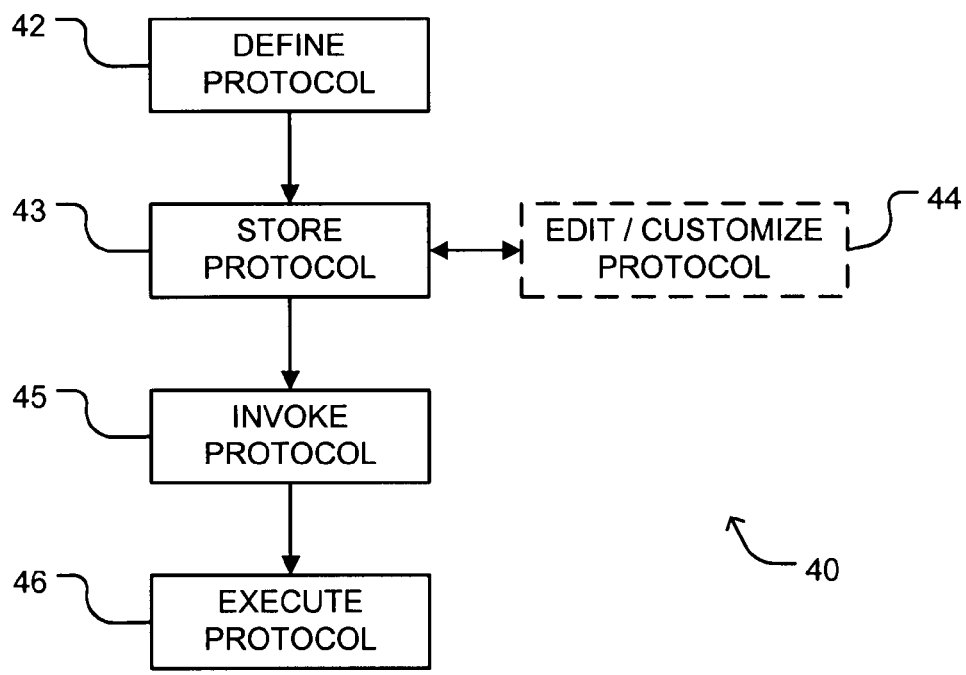
FIG. 2 is a flowchart illustrating a method for causing a medical ultrasound machine to perform a specific protocol.

FIG. 2 illustrates a method 40 for operating an ultrasound machine 10. In block 42 a protocol is defined. The protocol may be defined, for example, by an expert in ultrasound imaging who can define the setup to be used at each step of the protocol. The protocol definition may include any of:
  configuration choices that are not user-selectable at the time the protocol is executed;
  features that a user can control during execution of the protocol;
  limits on the extent which a user can control various features;
  etc.
The author of the protocol may specify which controls will be available to a user at each setup and what sequence of setups will be performed to complete the protocol. The output of block 42 may be a script that can be executed by a protocol controller of an ultrasound machine.

In some embodiments, block 42 is performed on an ultrasound machine, like ultrasound machine 10A. In other embodiments, block 42 is performed on separate apparatus, such as a programmed computer which executes protocol definition software. Where block 42 is performed on an ultrasound machine 10A, ultrasound machine 10A may have a training mode in which controls of a wide or full range of controls are available for selection.

In block 43, the protocol is saved and made available to an ultrasound machine. In block 44, a user may optionally edit or customize a protocol which has been saved.

In block 45, a user invokes the protocol. In some embodiments, the protocol is invoked automatically upon a user starting, logging into, or otherwise initializing an ultrasound machine. In other embodiments, a user is presented with a selection of two or more protocols and invoking the protocol may comprise selecting the protocol from among protocols available for selection. In some embodiments, a particular button on an ultrasound machine causes display of the protocols available for selection or a screen from which such protocols can be accessed.

In block 46 the protocol is executed. Block 46 results in the acquisition and display and/or storage of a number of (zero or more) ultrasound images as well as the acquisition and storage of a number of (zero or more) measurements.

In an example embodiment, a protocol is defined on an ultrasound machine like ultrasound machine 10A being operated in a training mode. In the training mode, an expert performs an exam using an ultrasound machine. All available controls are displayed. During the examination, the ultrasound machine records which controls are used at each stage. After the examination has been completed, the ultrasound machine creates a draft protocol in which only those controls used for each setup are displayed. In some embodiments, the expert user can indicate whether or not a setting should be fixed in the protocol or whether a control should be provided to enable a user of the protocol to change a value associated with the control. This permits an experienced user operating in the training mode to fully specify each setup while simplifying the selection of controls to be displayed to a user who uses the ultimate protocol. If desired, the draft protocol may be refined by loading the draft protocol into a protocol editor (which may be provided by the ultrasound machine or provided on a platform external to the ultrasound machine) and editing the draft protocol.

Figure 3:
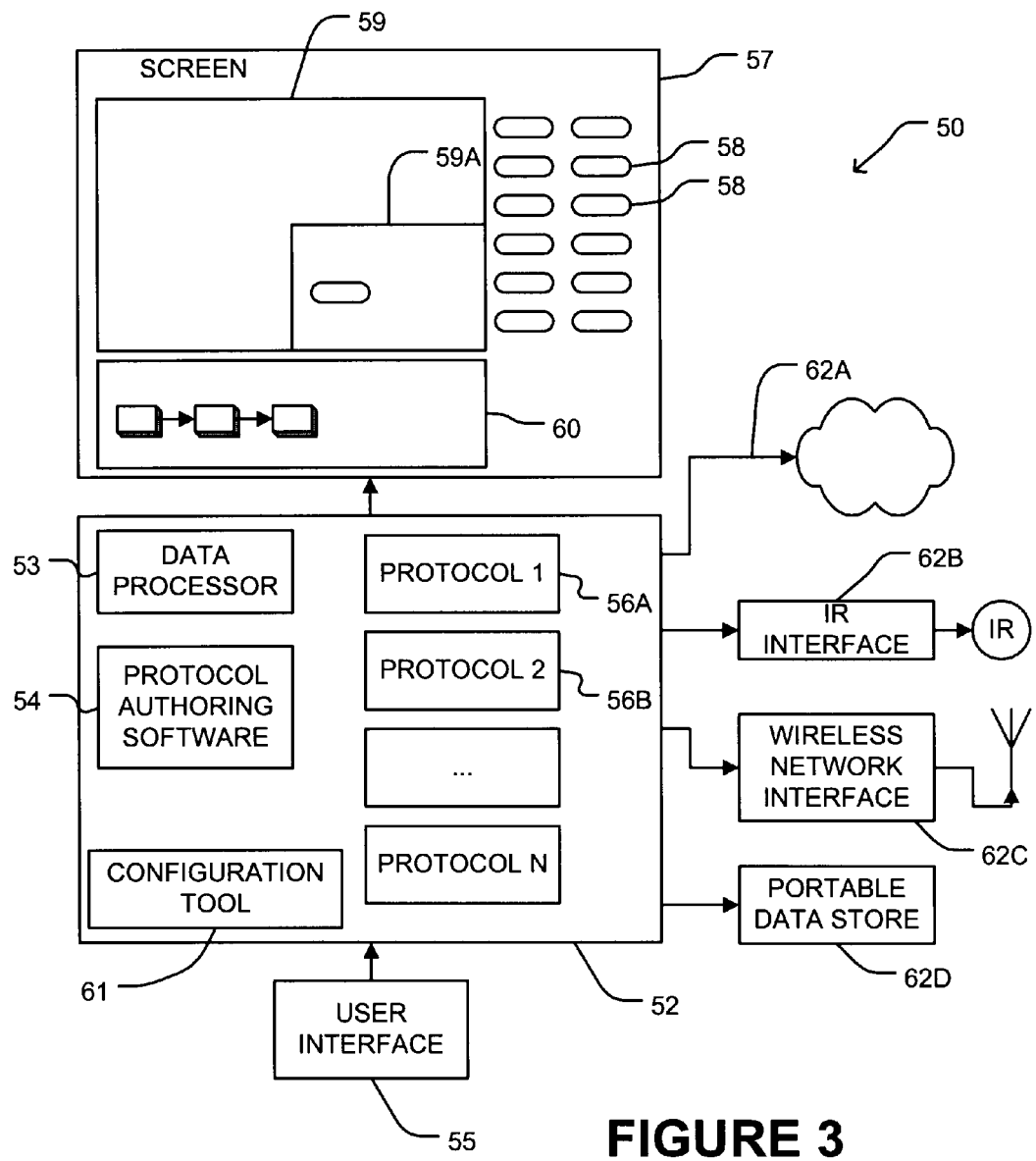
FIG. 3 is a schematic view of a system for developing new imaging protocols for a configurable ultrasound machine.

FIG. 3 shows an example apparatus 50 for defining protocols. Apparatus 50 may comprise a programmed computer 52 comprising a data processor 53, and a user interface 55 for interacting with computer 52. Computer 52 may execute protocol-authoring software 54 and store information defining one or more protocols 56 (individually numbered 56A, 56B, etc.) for delivery to an ultrasound machine (such as, for example, an ultrasound machine 10A).

A protocol 56 may be delivered to an ultrasound machine 10A in any of a wide range of ways. Illustrated schematically in FIG. 3 are:
- a direct wired connection, such as an ethernet or other network connection 62A;
- an infrared wireless connection 62B;
- a wireless networking connection 62C;
- a portable data store 62D or other computer-readable medium that can retrieve a copy of a protocol 56 from apparatus 50 and be physically carried to deliver the copy of the protocol to a configurable ultrasound machine.

In the ultrasound machine 10A illustrated in FIG. 1A, there is provided an interface 51 which can receive an incoming protocol 56 in the form of a script file and make that protocol available for execution by ultrasound machine 10A. Setups 35 required by a protocol may also be imported by way of interface 51.

In the illustrated embodiment, apparatus 50 includes a display 57 which includes graphical representations for a complete range of available controls 58 and an authoring area 59 into which a user who is defining a protocol can introduce and arrange different controls 58. Main controls for each setup (typically one or two controls) may be placed in a main control area 59A. Main control area 59A may comprise an area which is smaller than the total area of display 57, and may be located in authoring area 59 (as in the illustrated embodiment) or some other convenient location on display 57. Main control area 59A may be delineated by a boundary which separates main control area 59A from the rest of display 57 in some embodiments. When the protocol is executed on an ultrasound machine 10A the controls that have been selected as main controls will be displayed in main control area 59A of a display on the ultrasound machine 10A where they will stand out and be easy for a user to access. The main controls displayed in main control area 59A may be different in different steps of the protocol. For example, the main controls may adjust operating parameters of ultrasound machine 10A in some steps, may acquire images in other steps, and may take measurements or store data in other steps.

A user can generate a protocol by creating one or more setups. Each setup may include a configuration for an ultrasound machine and an arrangement of one or more controls 58 that will be made available to a user when the protocol is executed. A user of apparatus 50 may define a configuration for an ultrasound machine to be specified in a protocol by invoking a configuration tool 61 which provides (graphically, in text, or in some other representation) settings for parameters that control the operation of the ultrasound machine and allows the user to set those parameters to have desired values. Advantageously, configuration tool 61 permits users to access a range of pre-defined presets for creating setups. Each preset contains a set of parameters useful for configuring an ultrasound machine 10 to perform particular types of measurement. For example, presets may be provided for applications such as:
  imaging soft tissues;
  imaging musculo-skeletal features;
  special imaging modes such as Doppler imaging modes;
  etc.

In some cases a category may include a number of more specific presets. For example, several different presets may be provided for different musculo-skeletal imaging applications. By way of example only, there may be separate presets for imaging:
  angle
  knee
  shoulder
  wrist
  etc.

A user may adopt all of the parameter values specified by a preset, load a preset and then alter one or more parameter values to adjust the preset or set parameter values manually.

A user of apparatus 50 may define the selection and arrangement of controls that will be made available to a user of an ultrasound machine executing the protocol by, for example, placing prototype controls 58 onto area 59. The user can then define a complete protocol by specifying a sequence of one or more setups in area 60.

In some embodiments, a protocol can include sub-protocols. Such embodiments facilitate the reuse of all or portions of existing protocols to make new protocols. Such embodiments also facilitate the maintenance of protocols. In such embodiments a user of apparatus 50 may insert a call to invoke another protocol as a sub-protocol in a protocol being defined. When a protocol that includes a sub-protocol is executed, the sub-protocol is executed at an appropriate point. After the sub-protocol has completed executing, the protocol proceeds to the next setup (or sub-protocol) following the point at which the sub-protocol was invoked. In general, sub-protocols may operate in a manner analogous to subroutines in computer programming.

Figure 4:
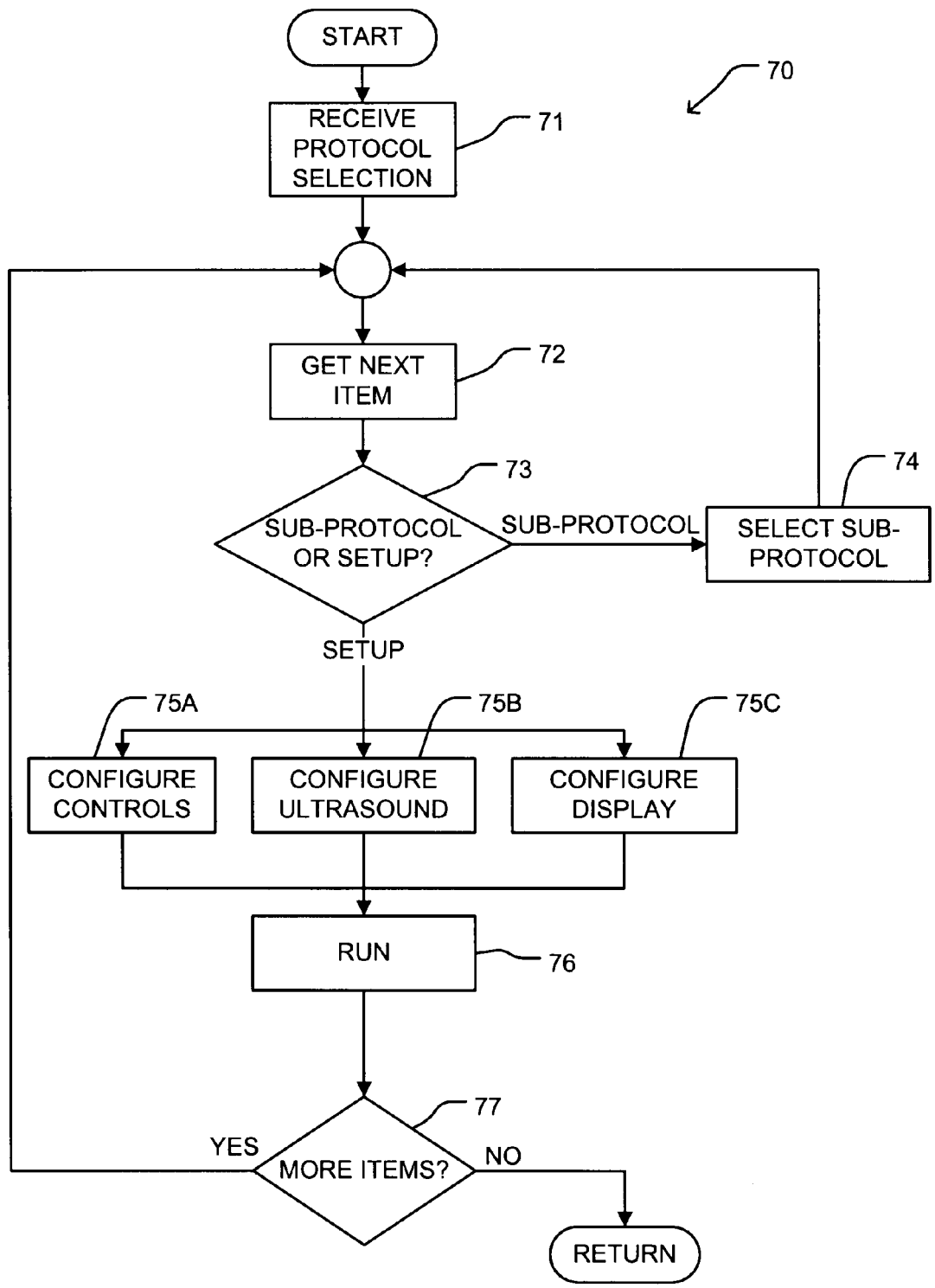
FIG. 4 is a flowchart illustrating a method for operating an ultrasound machine to perform an ultrasound protocol.

FIG. 4 illustrates a method 70 which may be invoked on an ultrasound machine to perform a previously-defined protocol. In block 71 a protocol selection is received. Where only one protocol is defined or available then block 71 is not necessary. In block 72 the next item (which will initially be the first item) of the selected protocol is obtained. Block 73 determines if the item is a sub-protocol or a setup. If the item is a sub-protocol, method 70 proceeds to block 74 where the sub-protocol is selected, then returns to block 72 to process the next (first) item of the selected sub-protocol. If the item is a setup, method 70 proceeds to one or more of blocks 75A-C, depending on the type of setup.

Blocks 75A, 75B, and 75C respectively configure the user controls, ultrasound transmission and reception, and display characteristics according to the current setup, which is initially the first setup. Blocks 75A, 75B and 75C may be performed in parallel, as shown in FIG. 4, or may be performed sequentially in any suitable order. In block 76 the current setup is run. Block 76 may, for example, configure operating the ultrasound machine to generate ultrasound as specified in block 75B, process the received ultrasound as specified in block 75B, configure display parameters as specified in block 75C and accept user input from controls provided according to configuration 75A. When block 76 has completed then method 70 continues to block 77 which determines whether the protocol (or sub-protocol) includes additional items. If yes, then method 70 returns to block 72 to process the next item. In the case of a sub-protocol, if block 77 determines that the sub-protocol has no more items then the main protocol, which called the sub-protocol, is checked at block 77 for additional items. If there are no more items then method 70 ends.

Block 76 may be determined to have completed based on one or more of a variety of different indications. These may include indications such as:
- a user activates a control which requests that the protocol move to the next setup;
- an image or other data required by the setup has been successfully received or saved;
- an operation specified by the setup (e.g. taking a specified measurement) has been completed; or
- the like.

Figure 5A:
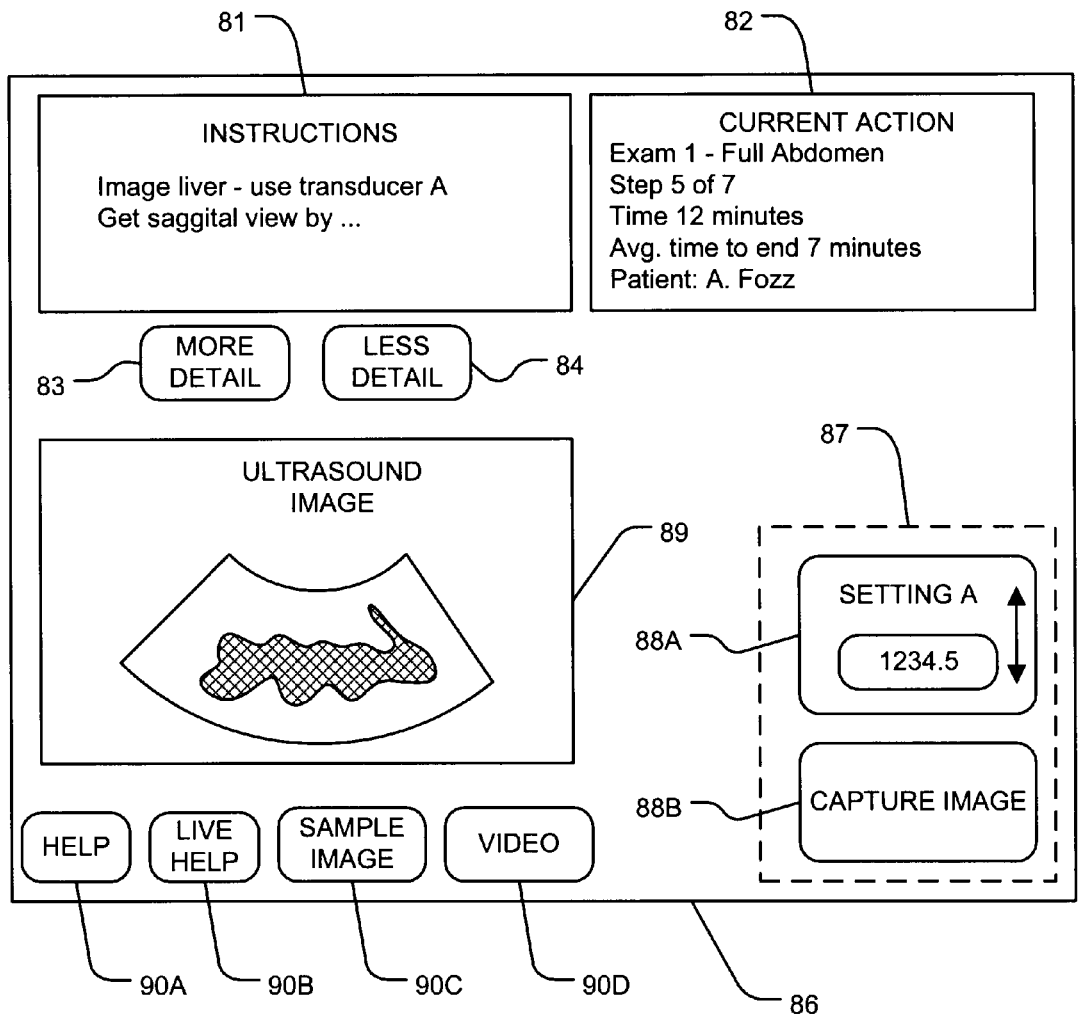
FIG. 5A is an example of a possible touchscreen display for an image acquisition phase of a protocol.

FIG. 5A shows a screen 86 that may be displayed during a procedure. Screen 86 includes a primary area 87 in which the main controls with which a user can interact to control aspects of operation of an ultrasound machine in the current setup can be displayed. In the illustrated embodiment, controls 88A and 88B are displayed in primary area 87. More or fewer controls could be displayed in any particular setup. In the illustrated embodiment a current parameter value corresponding to control 88A is displayed on the control 88A.

In the illustrated embodiment, screen 86 includes an image area 89. Where an ultrasound machine includes both a touch screen and an image display screen (for example in apparatus 10A of FIG. 1A which includes an image display screen 20A and a touch screen 32A) image area 89 may depict a version of the same image being shown on the image display screen. Screen 86 may also comprise an instruction area 81 wherein relevant instructions may be displayed, and a current action area 82 where information about the current action of the procedure being performed may be displayed. A more detail button 83 and a less detail button 84 may be provided for respectively increasing and decreasing the level of detail of instructions shown in instruction area 81.

Figure 5B:
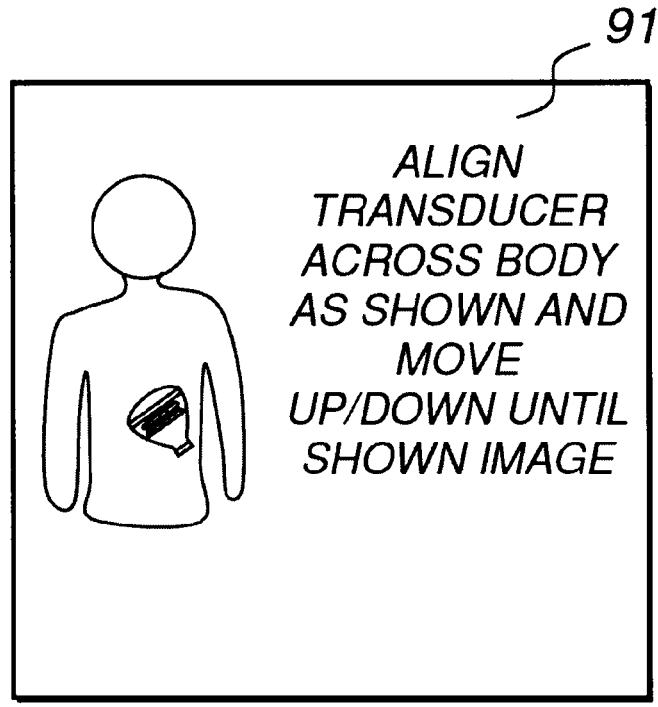
FIG. 5B is an example context-sensitive help screen for the protocol step illustrated in FIG. 5A.

Also provided in screen 86 are controls 90A, 90B, 90C and 90D which respectively link to help, live help, sample images, and video, each related to the current setup. For example, FIG. 5B shows a screen 91 that may be displayed in response to a user invoking help button 90A. Screen 91 includes text that explains to the user how to operate the ultrasound machine to acquire the information needed in the current setup and also includes a diagram that illustrates where and how to position an ultrasound transducer to acquire the necessary image. In environments where live help is available, the user could invoke control 90B to be connected by way of a suitable wired or wireless data communication network to a terminal manned by a person who can provide advice to the user. The user could invoke control 90C to see sample images which are suitable and/or unsuitable. The user can invoke control 90D to cause a short video to be shown. The video may illustrate how to properly manipulate a transducer and otherwise operate the ultrasound machine to acquire whatever image or other data is required for the current step. As one skilled in the art will appreciate, when a different procedure is being performed, different additional controls may optionally be provided outside of primary area 87, different text instructions may be provided and help sample image and video buttons linked to help sample images and video related to different setups than the setup to which example screen 86 corresponds.

Figure 6A:
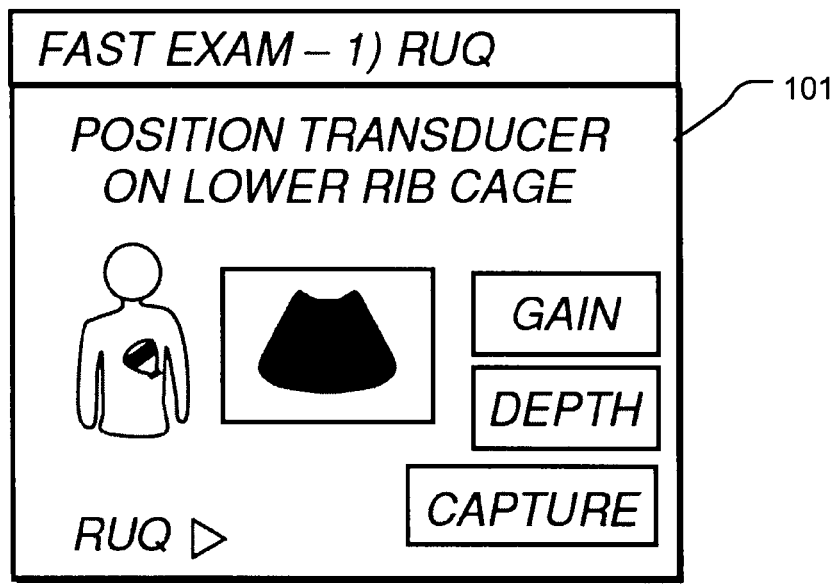
FIGS. 6A through 6D are example touchscreen displays for a number of successive stages in an example protocol for a focus assessment by sonography in trauma exam.
Figure 6B:
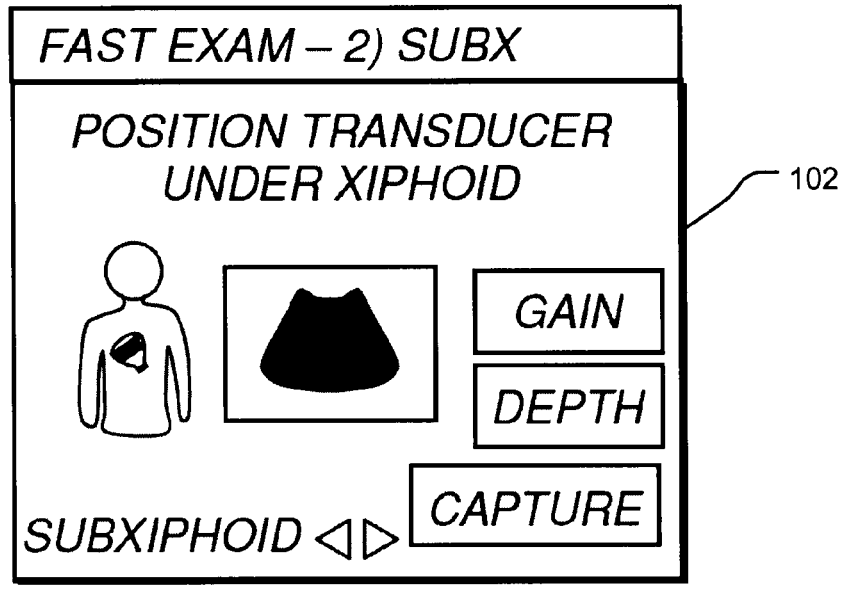
Figure 6C:
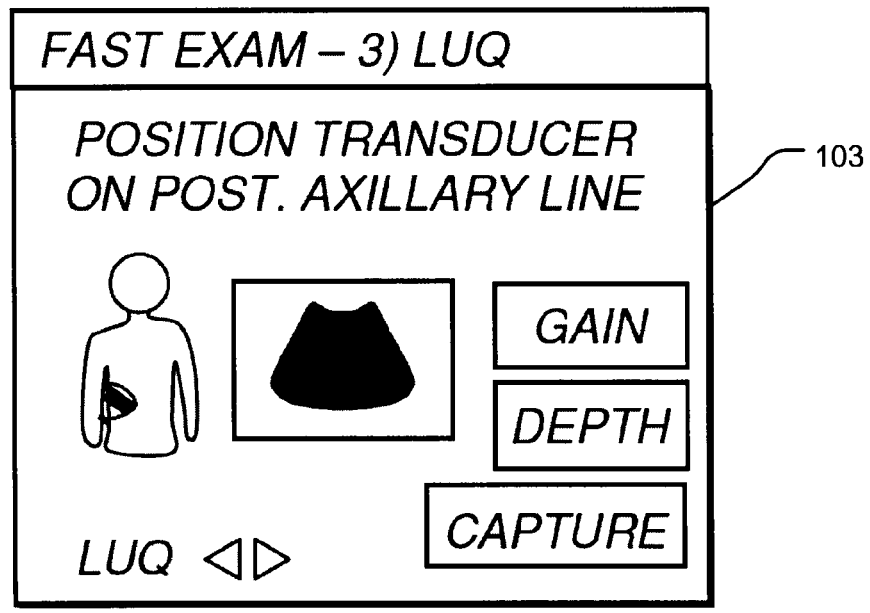
Figure 6D:
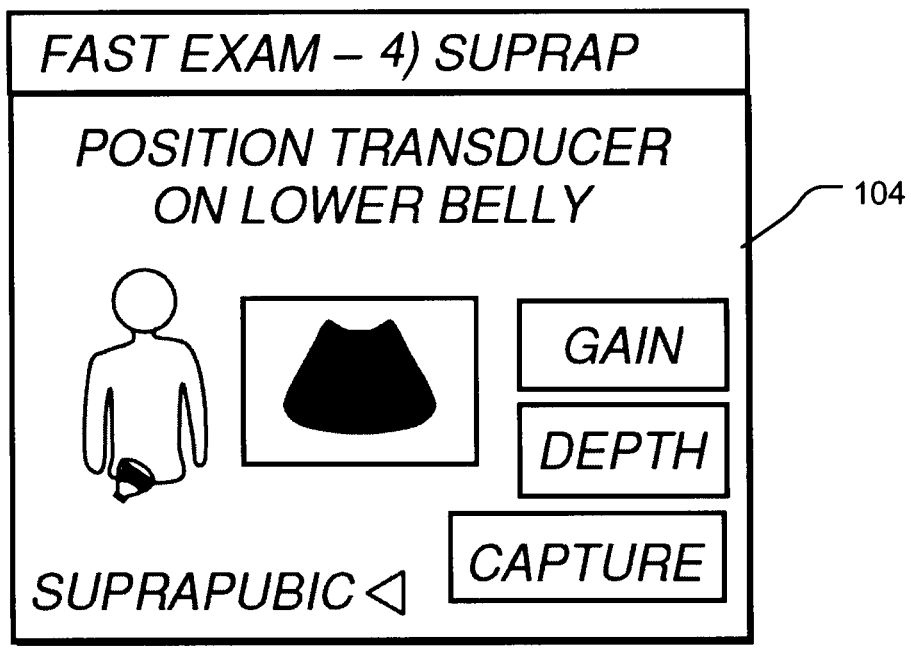
Figure 7A:
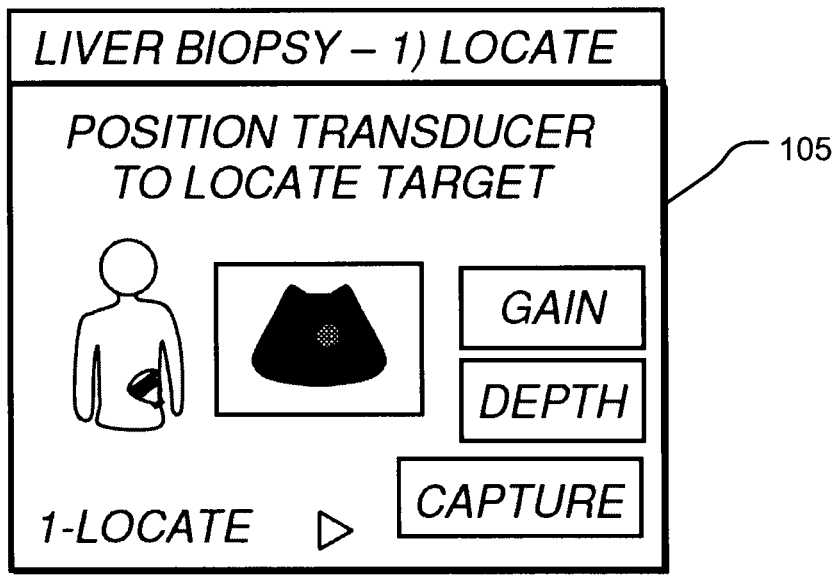
FIGS. 7A through 7C are example touchscreen displays for a number of successive stages in an example protocol for a freehand biopsy procedure.
Figure 7B:
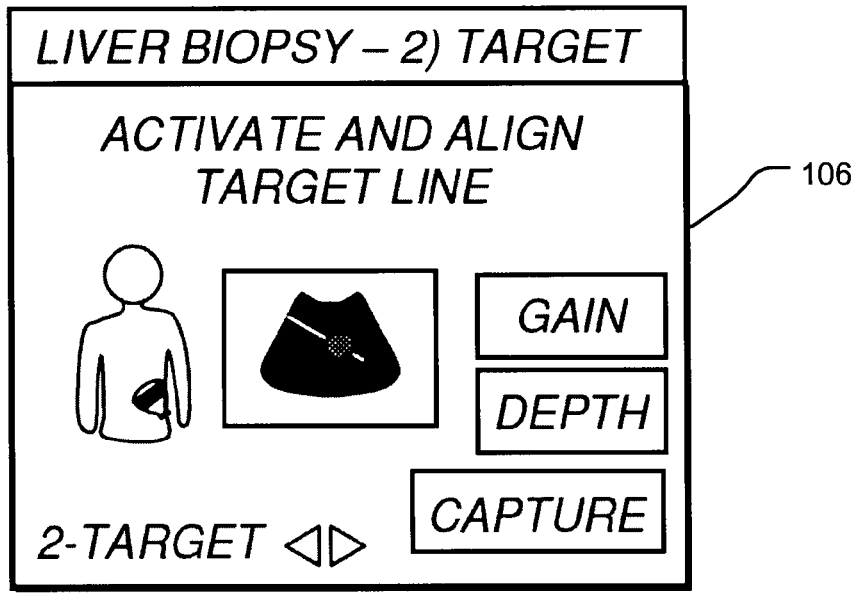
Figure 7C:
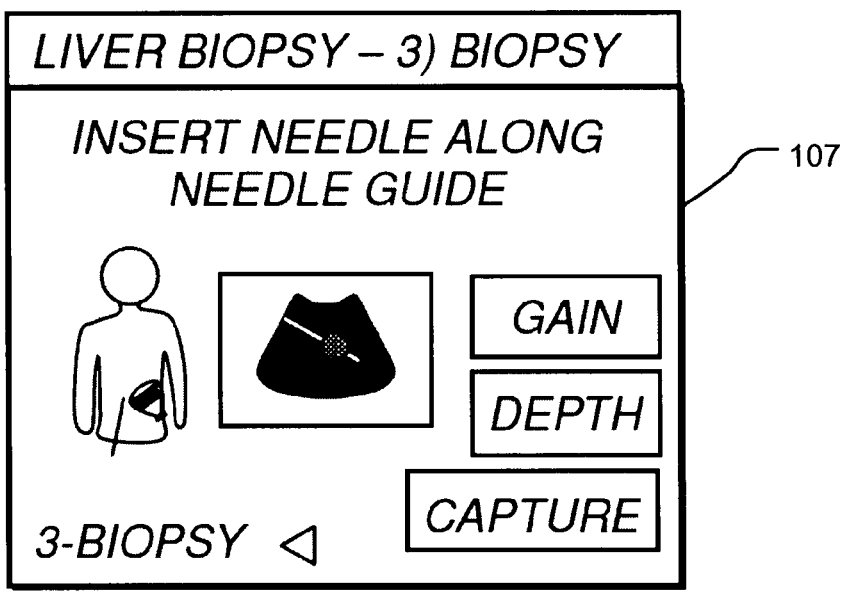

It can be appreciated that methods as described herein may be used to define protocols of arbitrary length and complexity and to lead users through the protocols. FIGS. 6A through 6D depict a set of screens which illustrate a sequence of steps that may be provided for a specific protocol for the purpose of a focus assessment by sonography in trauma (FAST) exam. FIG. 6A shows a screen 101 which may be displayed for scanning the right upper quadrant. FIG. 6B shows a screen 102 which may be displayed for scanning the subxiphoid area. FIG. 6C shows a screen 103 which may be displayed for scanning the left upper quadrant. FIG. 6D shows a screen 104 which may be displayed for scanning the suprapubic area. FIGS. 7A through 7C depict a set of screens which illustrate a sequence of setups that may be provided for a specific protocol for the purpose of a freehand liver biopsy procedure. FIG. 7A shows a screen 105 which may be displayed for positioning the probe to target a lesion. FIG. 7B shows a screen 106 which may be displayed for activating a needle guide. FIG. 7C shows a screen 107 which may be displayed for inserting a needle using the guide. Each of screens 101-107 shows the desired position of the probe and an example image, along with various controls and other information relevant to the current step of the procedure being performed.

In some embodiments, the selection and arrangement of controls for a particular setup may be defined in a markup language such as hypertext markup language (HTML) or extended markup language (XML). An ultrasound machine (for example, ultrasound machine 10A) may include browser software which reads the markup language and displays the specified controls on touch screen 32A according to the markup language.

The high degree of flexibility provided by the architecture described herein may permit protocols to be defined which vary based upon the level of experience of a user. The selection of an appropriate protocol may be manual. For example, a user may manually select between "basic" and "advanced" versions of the same protocol. In the alternative, the protocols may be made available to users based upon stored information regarding the level of experience possessed by the user. More rigid protocols may be provided for less experienced users. Protocols intended for more experienced users may be afforded more options for advanced control of the protocols. The availability of different protocols and/or the default selection of protocols may be defined at the user level. For example, each user could have a unique user profile, and an ultrasound machine may have a group of protocols to display for each user profile.

In some embodiments, the type of sample images provided may be selected based upon the type of patient. For example, different sample images may be displayed depending upon whether the subject is male or female. Different sample images may be displayed depending upon whether the subject is a child or an adult. Different sample images may be displayed depending upon whether the subject is obese or not. The sample images may be selected based upon information about a patient that has been input into or made available to an ultrasound machine in advance.

The available help may also be based upon characteristics of the patient. For example:
  if the patient is identified as being obese then the help selection may include specific help directed to obtaining satisfactory images from obese subjects;
  if the patient is identified as being a child then the help selection may include specific help directed to obtaining satisfactory images of pediatric subjects;
  etc.

Some ultrasound protocols require that various measurements be made of certain characteristics in ultrasound images. In some embodiments, a measurement control is provided. A person specifying a protocol can select the measurement control and then specify which measurements are to be made. The measurement control may, for example, include components capable of providing any of a wide range of different sorts of measurements. Some examples of measurements that a measurement control could be configured to provide are:
  the distance between two anatomical features depicted in an image;
  Doppler measurements at a point in an image;
  the volume of an organ or other anatomical structure;
  the perimeter of an organ or other anatomical structure;
  etc.

In some cases, the operation of a measurement control may be specified by a measurement template. The measurement template may permit the definition of custom measurements. An example of a custom measurement is a measurement for determining the volume of an organ such as the liver or heart based on three distance measurements. The measurement template may permit a name to be given to a custom measurement so that the custom measurement may be retrieved by name in future. The measurement template may also specify annotations (which could, for example, explain how to obtain the required measurement), pictograms and/or animations (which may illustrate how to obtain the required measurement).

Since a protocol can be defined as a sequence of different setups, it is not mandatory that the setups and the protocol be generated at the same time. Some embodiments permit a protocol to be created by selecting previously-defined setups and/or by selecting previously-defined protocols to be executed as sub-protocols. Previously-defined setups and/or other protocols can be organized in a desired sequence to be performed by the protocol. In some embodiments, a protocol may include conditional branches. Such conditional branches may be based upon outputs from previous setups. For example, if a certain measurement is in a defined range then the protocol may specify that other measurements should also be made, or other images should also be obtained. These additional measurements or images may not be required in other cases.

In some embodiments, a protocol can be defined prior to the definition of some or all of the setups. Such embodiments permit the overall structure of a protocol to be defined first and the individual setups to be defined later.

In some embodiments, an ultrasound machine is configured to record notes, comments, or other observations simultaneously with acquiring images. A record of the observations may be stored with the results of the protocol. Various interfaces may be provided to receive such observations. In some embodiments, for example ultrasound machine 10A of FIG. 1A, a user can bring up a worksheet on touch screen 32A while continuing to image on a main image display screen 20A. The user may enter information into the worksheet directly. For example, text may be entered using a keyboard connected to ultrasound machine 10A or a keyboard control displayed on touchscreen 32A.

In other cases, information may automatically be inserted into the worksheet. For example, where a particular measurement is specified by a protocol, the result of the measurement may automatically be entered into the worksheet. The worksheet may also include images and/or other information acquired by the protocol. This feature allows a detailed report in an electronic format to be generated automatically during the execution of the protocol. The overall format of the content of the report may be specified in advance and may be part of the protocol definition. The report may be printed out and/or stored electronically.

The visual manifestation of some controls may include image depictions. For example, a control for moving a focal zone or selecting a different biopsy target point may include a depiction of an ultrasound image. The focal zone or biopsy target point may be selected by touching an appropriate location on the image. Other manipulations, such as zooming, making an image lighter or darker, making image crisper, etc. may also be provided by touch screen manipulations.

In some embodiments, a persistent control bar is provided in a consistent location on the screen displayed by a protocol. The control bar permits a user to navigate through the execution of protocol steps.

In some embodiments, the controls available include a time gain control (TGC) panel. A TGC panel may permit a user to define a new TGC curve by tracing a finger across touch screen 32 at the location of the control.

In some embodiments, a presets panel is provided. A preset contains all the necessary imaging parameters to configure an ultrasound machine for a specific scan. The presets panel is a control that provides a set of presets for a specified application. For example, for a musculoskeletal application, the presets panel may provide ankle, knee, shoulder and wrist presets, among others. The presets panel allows the user to select any of the presets for the specified application.

In some embodiments, each setup corresponds to a particular state of an ultrasound system. The functionality available is different in each state. For example, the following table lists three groups of states:

| Imaging Mode States | Operation Mode States | Other Operation States |
|---|---|---|
| B mode | freeze | system menu |
| M Mode | measurements mode | protocol selection |
| dual mode | annotations mode | 3-D application |
| color Doppler mode | pictograms mode | reporting |
| power Doppler mode | arrow mode | patient ID |
| pulsed wave mode |  | patient review |
| continuous wave mode |  |  |
| 3-D/4-D mode |  |  |

A system may permit one state from each column to be active at the same time. The selection of a mode can drive the selection of a layout of controls displayed on a touch screen.

In the foregoing description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Certain implementations of the invention comprise computer processors which execute software instructions which cause the processors to perform a method of the invention. For example, one or more processors in an ultrasound machine may implement methods for executing protocols or defining protocols as described herein by executing software instructions in a program memory accessible to the processor(s). One or more processors in apparatus for defining protocols may perform protocol definition methods as described herein by executing software instructions in a program memory accessible to the processor(s).

Certain aspects of the invention may also be embodied in the form of a program product. The program product may comprise any tangible medium which carries a set of computer-readable signals comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The computer-readable signals on the program product may optionally be compressed or encrypted.

Where a component (e.g. a software component, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example, additional embodiments may be generated by making modifications, permutations, additions and sub-combinations of the features of the example embodiments described above.

What is claimed is:

1. A method for operating an ultrasound machine, the method comprising:
    performing a training mode ultrasound examination with the ultrasound machine in a training mode in which all available controls are displayed;
    recording, during the training mode ultrasound examination and by the ultrasound machine, which controls are used at each stage of the training mode ultrasound examination;
    creating, after completion of the training mode ultrasound examination, a custom protocol in which only those controls used for each stage of the training mode ultrasound examination are displayed;
    providing a plurality of protocols for the ultrasound machine, the plurality of protocols including the custom protocol, and each protocol of the plurality of protocols specifying a series of one or more ultrasound images to be acquired and step-by-step instructions for acquiring the one or more ultrasound images, wherein each protocol includes patient imaging configuration choices that are not user-selectable at the time the protocol is executed to image a patient, features that a user controls during execution of the protocol, and limits on an extent which the user controls various features;
    receiving subject information specifying one or more characteristics of a current subject of an ultrasound examination;
    determining a subset of the plurality of protocols based on the subject information, the subset including two or more of the plurality of protocols and including only protocols applicable to subjects having the one or more characteristics of the current subject of the ultrasound examination, wherein the two or more of the plurality of protocols include is the custom protocol;
    displaying the subset of the plurality of protocols to a user of the ultrasound machine;
    receiving a user-selected one of the displayed protocols, wherein the user-selected one of the protocols is the custom protocol; and
    executing the user-selected protocol, which activates the ultrasound machine to acquire an image and which visually displays a prompt via a display screen that provides the step-by-step instructions associated with the selected protocol to guide the user to acquire the one or more ultrasound images specified by the selected protocol, wherein the prompt includes information regarding a particular transducer to apply and how to make a particular measurement, and a graphical representation graphically showing how to apply the particular transducer to acquire an image.

2. A method according to claim 1 wherein the user selected protocol specifies a plurality of images to be acquired and comprises:
    a setup for each image to be acquired, each setup comprising configurations for the ultrasound machine; and
    one or more activities to be performed between acquiring images in the series of ultrasound images wherein, executing the user-selected protocol comprises operating the ultrasound machine to prompt the user to perform the one or more activities between acquiring the images.

3. A method according to claim 2 wherein the ultrasound machine has a touch screen display and the user-selected protocol comprises, for each image to be acquired and each activity to be performed between acquiring images, a layout of controls to be displayed on the touch screen display and the method comprises, for each of the images to be acquired and for each activity to be performed between images, displaying controls on the display according to the corresponding layout.

4. A method according to claim 3 wherein the user selected protocol defines, for each image to be acquired and each activity to be performed between acquiring images, one or more main controls for acquiring the image or performing the activity, and wherein the method comprises displaying main controls associated with each image to be acquired in a main control area of the touch screen display during acquisition of the image and the method comprises displaying in the main control area the main controls associated with the activity during performance of the activity.

5. A method according to claim 2 wherein the activity comprises making a measurement of an anatomical structure.

6. A method according to claim 5 wherein the measurement comprises a plurality of distance measurements between anatomical features depicted in ultrasound images.

7. A method according to claim 1 comprising defining the plurality of protocols wherein defining one of the plurality of protocols comprises providing a protocol editor and a plurality of setup files, wherein the protocol editor enables protocols to be defined by specifying a series of steps and selecting a setup file for each of the series of steps.

8. A method according to claim 7 wherein defining a protocol comprises invoking another protocol as a sub protocol.

9. A method according to claim 7 wherein defining a protocol comprises specifying one or more conditional steps, wherein the one or more conditional steps are configured only to be executed when a predetermined result occurs in one or more previous steps.

10. A method according to claim 1 wherein the one or more characteristics comprises a gender of the current subject.

11. A method according to claim 1 wherein the one or more characteristics comprises an age of the current subject.

12. A method according to claim 1 wherein the one or more characteristics comprises a height and weight of the current subject.

13. A method according to claim 1 wherein executing the user-selected protocol comprises displaying a visual record of an acquisition of at least one of the series of one or more ultrasound images specified by the user selected-protocol for a reference subject having the one or more characteristics of the current subject.

14. A method according to claim 1 comprising receiving user information specifying an experience level of a user of the ultrasound machine, wherein the determining the subset is based on the user information.

15. A method according to claim 14 wherein the plurality of protocols comprise an advanced version and a basic version of each protocol, and wherein displaying the subset comprises for each protocol, displaying only the basic version unless the user has an experience level exceeding a predetermined threshold experience level.

16. A method according to claim 1 wherein the user-selected protocol requires the user to acquire a sequence of two or more ultrasound images of more than one internal organ of the subject and the step-by-step instructions specified by the protocol guide the user to acquire each of the two or more ultrasound images, wherein the step-by-step instructions comprise instructing a user to use one type of probe for acquiring one of the images and another type of probe for acquiring another one of the images.

17. A method according to claim 1 wherein the user-selected protocol comprises a plurality of example images and executing the user-selected protocol comprises displaying an acquired image and a corresponding example image at the same time to permit a user to compare the acquired image to the corresponding example image.

18. A method according to claim 17 wherein the user-selected protocol comprises a plurality of sets of example images each associated with a corresponding set of one or more subject characteristics and the method comprises automatically selecting one of the sets of example images based on the characteristics of the current subject and displaying the example images from the automatically selected set of example images.

19. A method according to claim 18 wherein the plurality of sets of example images includes at least one set of child example images, one set of adult example images, one set of male example images, and one set of female example images.

20. A method according to claim 1, wherein the configuration choices that are not user-selectable at the time the protocol is executed are not user-selectable to all users of the ultrasound machine.

21. A method according to claim 1, wherein executing the user-selected protocol executes a script which causes the ultrasound machine to be placed in a succession of different configurations and to acquire and at least one of store or display ultrasound data for each of the configurations.

22. A method according to claim 1, wherein the prompt includes a series of images that are sequentially displayed, one after the other, each graphically showing a next different position of the transducer relative to the subject for a different image of the protocol.

23. A method according to claim 1, wherein the prompt includes a series of screens sequentially displayed, which instruct a user to activate a needle guide and insert a needle along the guide.

24. A method according to claim 23, wherein the protocol requires the user to make measurements of anatomical features imaged in the images.

25. A method according to claim 24, wherein the prompts include an image showing how to make the measurement.

26. Apparatus for operating an ultrasound machine, the apparatus comprising
   a data store;
   a processor and a display;
   the data store comprising a plurality of protocols for the ultrasound machine, each protocol specifying a series of one or more ultrasound images to be acquired and step-by-step instructions to acquire the one or more ultrasound images, wherein each protocol includes at least one of configuration choices that are not user-selectable at the time the protocol is executed, features that a user controls during execution of the protocol, or limits on an extent which the user controls various features; and
   the processor configured to:
   record, during a training mode ultrasound examination in which all available controls are displayed, which controls are used at each stage of the training mode ultrasound examination;
   create, after completion of the training mode ultrasound examination, a custom protocol in which only those controls used for each stage of the training mode ultrasound examination are displayed;
   receive subject information specifying one or more characteristics of a subject of an ultrasound examination;
   determine a subset of the plurality of protocols, the plurality of protocols including the custom protocol, based on the subject information, the subset including only protocols applicable to subjects having the one or more characteristics of the subject of the ultrasound examination; cause the display to display the subset to a user of the ultrasound machine;

receive a user-selected one of the subset of protocols; and execute the user-selected protocol, which activates the ultrasound machine to acquire an image and which visually displays a prompt via a display screen that provides the step-by-step instructions to guide the user to acquire the one or more ultrasound images, wherein the prompt includes information regarding a particular transducer to apply and how to make a particular measurement, and a graphical representation graphically showing how to apply the particular transducer to acquire the one or more images.

* * * * *